(12) United States Patent
Yang et al.

(10) Patent No.: US 12,203,918 B2
(45) Date of Patent: Jan. 21, 2025

(54) PREDICTION OF RESERVOIR FLUID PROPERTIES FROM MUD-GAS DATA

(71) Applicant: Equinor Energy AS, Stavanger (NO)

(72) Inventors: Tao Yang, Stavanger (NO); Ibnu Hafidz Arief, Oslo (NO); Martin Niemann, Oslo (NO); Thibault Forest, Sandnes (NO); Knut Kristian Meisingset, Hafrsfjord (NO)

(73) Assignee: Equinor Energy AS, Stavanger (NO)

( * ) Notice: Subject to any disclaimer, the term of this patent is extended or adjusted under 35 U.S.C. 154(b) by 511 days.

(21) Appl. No.: 17/437,963

(22) PCT Filed: Mar. 13, 2020

(86) PCT No.: PCT/NO2020/050071
§ 371 (c)(1),
(2) Date: Sep. 10, 2021

(87) PCT Pub. No.: WO2020/185094
PCT Pub. Date: Sep. 17, 2020

(65) Prior Publication Data
US 2022/0163503 A1 May 26, 2022

(30) Foreign Application Priority Data
Mar. 13, 2019 (GB) .................................... 1903444

(51) Int. Cl.
*G01N 33/24* (2006.01)
*G06N 20/00* (2019.01)
(52) U.S. Cl.
CPC .......... *G01N 33/241* (2013.01); *G06N 20/00* (2019.01)

(58) Field of Classification Search
CPC . G01R 33/448; G01R 33/241; G01R 33/0036
See application file for complete search history.

(56) References Cited

U.S. PATENT DOCUMENTS

2018/0088096 A1* 3/2018 Ritzmann ............ G01R 33/448

FOREIGN PATENT DOCUMENTS

| CN | 104849365 A | * | 8/2015 |
| WO | 2009035918 A1 | | 3/2009 |

(Continued)

OTHER PUBLICATIONS

May 18, 2020—(WO) International Search Report and Written Opinion—App PCT/NO2020/050071.
Jul. 19, 2019—(GB) Search Report—App 1903444.6.

*Primary Examiner* — Lam S Nguyen
(74) *Attorney, Agent, or Firm* — Banner & Witcoff, Ltd.

(57) ABSTRACT

The present disclosure relates to techniques for prediction of reservoir fluid properties of a hydrocarbon reservoir fluid, such as the density, the saturation pressure, the formation volume factor and the gas-oil ratio of the reservoir fluid. To predict the reservoir fluid properties, a model is generated by selecting a subset of available reservoir samples based on a degree of biodegradation of the samples, generating an input data set comprising input data and target data, the input data comprising measured or predicted mud-gas data; and generating a model using the input data. The application of this technique allows a continuous log of the selected property to be generated using mud-gas data collected during the well drilling process.

2 Claims, 7 Drawing Sheets

(56) References Cited

FOREIGN PATENT DOCUMENTS

| WO | 2009142873 | A1 | 11/2009 |
| WO | 2010039566 | A1 | 4/2010 |
| WO | 2015047249 | A1 | 4/2015 |
| WO | 2017139271 | A2 | 8/2017 |
| WO | 2018170035 | A1 | 9/2018 |

* cited by examiner

PREDICTION OF RESERVOIR FLUID PROPERTIES FROM MUD-GAS DATA

The present application is a U.S. National Phase of International Application No. PCT/NO2020/050071, filed on Mar. 13, 2020, designating the United States of America and claiming priority to United Kingdom Patent Application No. 1903444.6, filed on Mar. 13, 2019. This application claims priority to and the benefit of the above-identified applications, which are fully incorporated by reference herein in their entirety.

The present disclosure relates to techniques for prediction of reservoir fluid properties of a hydrocarbon reservoir fluid, such as the density, the saturation pressure, the formation volume factor and the gas-oil ratio of the reservoir fluid.

Hydrocarbon reservoirs are typically composed of a mixture of different hydrocarbons, commonly from $C_1$ to $C_{36+}$, as well as other fluids such as water, sour gases (e.g. $CO_2$ and $H_2S$) and other gases (He and $N_2$). During hydrocarbon exploration, it is desirable to identify the reservoir fluid properties of a new reservoir at the earliest stage possible.

Before drilling a well, various surveys may be undertaken to identify potential hydrocarbon reservoirs. Such surveying may include gravity surveying, electromagnetic surveying and seismic surveying. Surveying data can provide a good indicator of the likelihood of a hydrocarbon-bearing reservoir, but is not effective for predicting the fluid properties of the reservoir. In order to do this, it is usually required to drill a well and take physical samples.

Once a well has been completed, it is possible to collect samples of the reservoir fluid during well testing or production. However, this traditional approach provides reservoir fluid data too late for it to be used to inform decisions made before well test and production.

Three techniques are used commonly used today to analyse the reservoir and provide early stage analysis of the reservoir fluid properties. These are logging while drilling (LWD), mud-gas logging, and downhole fluid sampling.

LWD is a technique in which downhole well logging tools are provided within the well borehole, typically within a drilling collar. These tools perform testing as drilling occurs, which may include: gamma ray (GR) logging, which is used to characterise the rock or sediment in the borehole (e.g. sand or shale); neutron density logging, which measures the hydrogen index (HI) in a reservoir, which is directly related to porosity; and resistivity logging, which measures the electrical resistivity to determine the presence of water or hydrocarbons.

LWD provides continuous logging data for the entire well and can provide probabilistic estimates of reservoir composition based on the geology. However, LWD it is not able to directly distinguish between different hydrocarbons. Additionally, the LWD tools are expensive and consume significant rig time during the drilling process.

Sampling while drilling (SWD) is a form of LWD in which fluid samples are taken while drilling. However, such operations cost rig time and the resulting samples typically have high contamination from the drilling mud.

Mud-gas logging is a technique in which hydrocarbon gas is released from drilling mud at the surface and then examined. When drilling into the reservoir, a small quantity of the reservoir fluid will be carried in the drilling mud to the surface. At the surface, the drilling mud is processed to release a mixture of gases, known as "mud gas", which is then examined to estimate certain properties of the reservoir.

At reservoir conditions, the reservoir fluid can be reservoir gas or reservoir oil. Mud gas only contains the light, gaseous fractions, which are usually from $C_1$ to $C_5$, but can sometimes go up to $C_7$ to $C_8$ with certain tools. Mud gas does not contain extensive information of oil components, which are usually $C_7$ to $C_{38+}$.

This type of logging is commonly used to determine when the well bore is in the correct zone, i.e. within a hydrocarbon-bearing zone of a reservoir.

Mud gas is often $C_1$ rich and the composition is not comparable with reservoir fluid composition, even for $C_1$ to $C_5$. However, certain corrections may be performed in order to estimate the $C_1$ to $C_5$ composition of the reservoir fluid based on the $C_1$ to $C_5$ composition of the mud gas.

Down hole fluid sampling is the most accurate way to determine the composition of the well. In this technique the drilling is suspended and a sampling tool is run into the well, e.g. on wireline, so that a sample of the reservoir fluid can be collected from the well. These samples are often sent to a laboratory where the sample is analysed and the detailed composition of the fluid is determined.

Whilst this technique is highly accurate, it is comparatively slow and so cannot provide immediate feedback during the wireline operation. Furthermore, the process is not continuous, and frequent sampling operations will increase the cost of the wireline operation and also related rig time. For real time fluid analyses, it is possible to use a downhole fluid analyser (DFA) to provide quick fluid property measurement. Such measurement is also not continuous and the related geo-operation cost is high.

All of the above techniques are often used in combination when drilling a new well. However, a need still exits for an improved technique for estimating properties of the reservoir fluid at an early stage of the procedure.

The present disclosure recognises that mud-gas data can in fact be used to accurately predict fluid properties of the reservoir that are influenced by the oil-related components, such as a gas-oil ratio, hydrocarbon fluid density at reservoir conditions, the saturation pressure and the formation volume factor.

Viewed from a first aspect, the present disclosure provides a method of generating a model for predicting at least one property of a fluid at a sample location within a hydrocarbon reservoir, comprising: providing an initial data set relating to a first plurality of sample locations, the initial data set comprising reservoir fluid properties data for each sample location; selecting a second plurality of sample locations as a subset of the first plurality sample locations, the selection being based on a degree of biodegradation of a fluid at the sample location; generating an input data set comprising input data and target data, the input data comprising (measured or estimated) mud-gas data, or a derivative thereof, for the second plurality of sample locations, and the target data comprising the at least one property of the hydrocarbon reservoir for each of the second plurality of sample locations; and generating a model using the screened data set such that the model can be used to predict the at least one property of the fluid at the sample location based on measured mud-gas data for the sample location.

It has been identified that samples taken at locations where the reservoir fluid has been bio-degraded have a $C_1$ to $C_5$ composition of the reservoir that more closely resembles the composition of a lean, gas reservoir, even when the reservoir may have a relatively high gas-oil ratio. As only these lighter hydrocarbons are detected by mud-gas logging, the incorporation of this data in the modelling process was found to disrupt the process to such an extent that the resulting model had too great an error to be usable. It has been found that by excluding this data, it is possible to generate a model for predicting properties of the reservoir fluid with high accuracy.

The method is preferably a computer-implemented method, and generating the model may comprise instructing a machine learning algorithm to generate the model using the screened data such that the model can be used to predict the at least one property of the fluid at the sample location based on measured mud-gas data for the sample location.

The at least one property is preferably a property influenced by the oil-related components of the fluid. That is to say, a property that not solely the product of the gaseous hydrocarbons within the fluid, whose composition can be predicted based on the mud-gas data.

The at least one property may comprise a density of the fluid at the sample location. It will be appreciated that the density may be calculated either at atmospheric conditions or reservoir conditions (e.g. taking into account the oil formation volume factor).

The at least one property may comprise a gas-oil ratio. That is to say, a ratio between the quantity of gaseous hydrocarbon and the quantity of liquid hydrocarbon. The gas-oil ratio is preferably a volume ratio. The gas-oil ratio may be a single-flash gas-oil measurement. However, any suitable gas-oil measurement may be used.

The at least one property may comprise a saturation pressure of the fluid at the sample location. That is to say, the pressure at which a secondary phase will appear with pressure depletion.

The at least one property comprises a formation volume factor of the fluid at the sample location. That is to say, the ratio of the volume of the fluid at reservoir (in-situ) conditions to the volume of the fluid at surface conditions. The at least one property may comprises a concentration of a hydrocarbon within the fluid at the sample location. The hydrocarbon may be a hydrocarbon that is not included within the mud-gas data. For example, the hydrocarbon may be a $C_{7+}$ hydrocarbon. That is to say, the hydrocarbon may be a $C_7$ hydrocarbon or may be a hydrocarbon heavier that $C_7$, e.g. a $C_8$ or heavier hydrocarbon. The hydrocarbon may be a hydrocarbon that is substantially an oil at reservoir conditions. The concentration of the hydrocarbon may be an absolute concentration (e.g. a molar concentration), or may be a relative concentration (e.g. a ratio compared to $C_1$), or may be an otherwise normalised concentration.

The reservoir may be a natural gas reservoir, a multiphase reservoir or an oil reservoir.

The reservoir fluid properties data may comprise measured composition data for a fluid at the sample location. The reservoir fluid properties data may contain the composition of $C_1$ to $C_{7+}$ hydrocarbons at the sample location, and preferably $C_1$ to $C_{20+}$ hydrocarbons, and more preferably $C_1$ to $C_{36+}$ hydrocarbons at the sample location. As used herein, the "$C_{x+}$" notation should be understood as meaning $C_x$ hydrocarbon or a heavier hydrocarbon.

The initial data set may comprise measured mud-gas data for the sample location. The input data may be the measured mud-gas data, or a derivative thereof, for the respective sample location. However, in some embodiments, this may not be required, for example where the model is generated based on estimated mud-gas data derived from the reservoir fluid properties data, and particularly measured composition data, for a fluid at the sample location.

The measured mud-gas data may be indicative of a composition of gases released from drilling fluid used whilst drilling through the sample location (i.e. passing through a drill bit performing the drilling). The measured mud-gas data may be indicative of a concentration of at least $C_1$ to $C_4$ gaseous hydrocarbons, and preferably at least $C_1$ to $C_5$ gaseous hydrocarbons.

The measured mud-gas data may comprise corrected, measured mud-gas data. The corrected, measured mud-gas may be corrected so as to correspond to the gaseous hydrocarbon composition of the fluid at the sample location. The correction may comprise a drilling fluid recycling correction, which may remove errors due to gases released from previous drilling operations due to recycling of the drilling fluid. The correction may comprise an extraction efficiency correction, which may remove errors due to the ability of the drilling fluid to carry different hydrocarbons.

In some embodiments, the input data may comprise estimated mud-gas data. The measured mud-gas data may comprise estimated, corrected mud-gas data. The estimated mud-gas data may be determined based on the reservoir fluid properties data for the sample location, and particularly may be based on a gaseous hydrocarbon composition of the fluid at the sample location. For example, the $C_1$ to $C_5$ composition of the fluid at the sample location, which may be determined from the reservoir fluid properties data.

Generating the model may comprise: training a machine learning algorithm with a first subset of the training data set; and testing the machine learning algorithm with a second, disjoint subset of the training data set. The first subset preferably comprises at least 50% of the samples of the training data set. The second subset preferably comprises at least 10% of the samples of the training set.

The input data of the first subset of the training data set may comprise estimated mud-gas data, or a derivative thereof, which may be derived from the reservoir fluid properties data. That is to say, the machine learning algorithm may generate a model to predict the fluid property from measured data, where the model is generated (only or significantly) based on data derived from the reservoir fluid properties data. Thus, measured mud-gas data is not required for all of the samples. That is to say, in some embodiments, measured mud-gas data or a derivative thereof, may not be available for one or more of the sample locations of the first subset of the training data set. The estimated mud-gas data is preferably estimated, corrected mud-gas data.

The input data of the second subset of the training data set comprises measured mud-gas data, or a derivative thereof. Preferably, the test data of the second subset of the training data set uses corrected, measured mud-gas data. In some embodiments, the test data of the second subset of the training data set may comprise measured mud-gas data, or a derivative thereof for some of the sample locations, and may comprise estimated mud-gas data, or a derivative thereof, for others of the sample locations.

The second plurality of sample locations preferably does not comprise sample locations where a degree of biodegradation exceeds a predetermined threshold. Preferably, the second plurality of sample locations does not comprise sample locations where any biodegradation is detected.

Biodegradation may be determined by detection of the presence of one or more microorganisms causing biodegradation. Biodegradation may be determined by analysis of a composition of the fluid, and particularly the compositions of the various hydrocarbons within the reservoir. In one example, biodegradation may be determination by determining that a ratio of $i\text{-}C_4/n\text{-}C_4$ is above a predetermined threshold and/or that a ratio of $i\text{-}C_5/n\text{-}C_5$ is above a predetermined threshold.

Viewed from a second aspect, the present invention provides a computer-based model for predicting at least one property of a fluid at a sample location within a hydrocarbon reservoir based on measured mud-gas data for that sample location, the computer-based model having been generated by the method above.

Viewed from third aspect, the present invention provides a tangible computer-readable medium storing the computer-based model.

Viewed from a fourth aspect, the present invention provides a method of predicting a value of a property of a fluid at a sample location within a hydrocarbon reservoir, the method comprising: providing measured mud-gas data for the sample location; and predicting the value of the property of the fluid at the sample location by supplying the measured mud-gas data to the computer-based model.

The method may further comprise determining a quality for the measured mud-gas data.

The method may further comprise providing an indication of confidence associated with the predicted value of the fluid property. The indication of confidence may be a numerical indication, but other indications may be used, such as colour indications (e.g. red/yellow/green), or word indications (e.g. "good"/"bad").

The indication of confidence may be based on a quality of the measured mud-gas data.

For a single data point, the indication of confidence may be reduced by one or more of a $C_1$, $C_4$ or $C_5$ concentration that is below a respective predetermined threshold.

Where mud-gas data is taken at a series of locations at different depths, the indication of confidence may be reduced by fluctuations of a component concentration of the mud-gas data greater than a threshold amplitude within a predetermined depth range.

Where mud-gas data is taken at a series of locations at different depths, the indication of confidence may be reduced by the missing of a predetermined number of preceding measurements or over a predetermined depth range.

The method may further comprise determining whether the fluid has been biodegraded by comparison of a ratio of i-$C_4$/n-$C_4$ to a predetermined threshold and/or comparison of a ratio of i-$C_5$/n-$C_5$ to a predetermined threshold. The predicting may be carried out after determining that the fluid has not been biodegraded. The determination may comprise that determining that the ratio of i-$C_4$/n-$C_4$ or i-$C_5$/n-$C_5$ is above the respective predetermined threshold.

The method may further comprise providing an indication of confidence associated with the predicted value of the fluid property. The indication of confidence may be based on whether the fluid has been biodegraded.

Viewed from a fifth aspect, the present invention provides a method of predicting a value of a fluid property of a fluid along a length of a well through a hydrocarbon reservoir, the method comprising: predicting a value of a fluid property of a fluid at a plurality of sample locations along a length of a well using the method above.

The method may further comprise: sampling a fluid at a sample location along a length of a well; determining a value of the fluid property of the fluid at the sample location, based on the sampling of the fluid; and adjusting the predicted values of the fluid property at one or more of the sample locations based on the determined value of the fluid property.

The method may further comprise: identifying that the fluid at one or more of the sample locations has been biodegraded, for example by determining that a ratio of i-$C_4$/n-$C_4$ or a ratio of i-$C_5$/n-$C_5$ from the measured mud-gas data exceeds a respective predetermined threshold; and generating a log from the predicted values for the plurality of sample locations, excluding the samples locations where the fluid is identified to be biodegraded. Alternatively, those data points may be included, but an indication of confidence may be provided for those samples, which may indicate low confidence in the predicted value.

The method may comprise: displaying, using an electronic display screen, a graph plotting one or both of the predicting value and the adjusted predicted value of the fluid property against a location of the respective sample location for each of the plurality of sample locations along the length of the well.

The method may further comprise: indicating, using the electronic display screen, an indication of confidence associated with one or more of the predicted value. For example, the indication of confidence may be illustrated numerically, verbally, chromatically or iconographically.

The method described above is preferably applied to a machine learning algorithm. However, it will be appreciated that the removal of bio-degraded samples from the data may facilitated improvements in models generated using other processes. Thus, viewed from a sixth aspect, the invention may provide a method of generating a model for predicting at least one property of a fluid at a sample location within a hydrocarbon reservoir, comprising: providing an initial data set relating to a first plurality of sample locations, the initial data set comprising reservoir fluid properties data for each sample location; selecting a second plurality of sample locations as a subset of the first plurality sample locations, the selection being based on a degree of biodegradation of a fluid at the sample location; generating an input data set comprising input data and target data, the input data comprising mud-gas data, or a derivative thereof, for the second plurality of sample locations, and the target data comprising the at least one property of the hydrocarbon reservoir for each of the second plurality of sample locations; and correlating the input data against the target data set to generate a model that can be used to predict the at least one property of the fluid at the sample location based on measured mud-gas data for the sample location.

The method may be a computer-assisted method. The step of selecting may be performed by a computing. The step of generating the input data set may be performed by a computing. The step of correlating may be performed by a computer.

All of the method described above, i.e. the methods of the first, fourth, fifth and six aspects may be performed in any suitable and desired way and on any suitable and desired platform. In a preferred embodiment the methods are each a computer-implemented method, e.g. the steps of the method are performed by processing circuitry.

The methods in accordance with the present invention may be implemented at least partially using software, e.g. computer programs. It will thus be seen that when viewed from further aspects the present invention provides computer software specifically adapted to carry out the methods described herein when installed on a data processor, a computer program element comprising computer software code portions for performing the methods described herein when the program element is run on a data processor, and a computer program comprising code adapted to perform all the steps of a method or of the methods described herein when the program is run on a data processing system.

The present invention also extends to a computer software carrier comprising such software arranged to carry out the steps of the methods of the present invention. Such a computer software carrier could be a physical storage medium such as a ROM chip, CD ROM, DVD, RAM, flash memory or disk, or could be a signal such as an electronic signal over wires, an optical signal or a radio signal such as to a satellite or the like.

It will further be appreciated that not all steps of the methods of the present invention need be carried out by computer software and thus from a further broad embodiment the present invention provides computer software and such software installed on a computer software carrier for carrying out at least one of the steps of the methods set out herein.

The present invention may accordingly suitably be embodied as a computer program product for use with a computer system. Such an implementation may comprise a series of computer readable instructions, which may be fixed on a tangible, non-transitory medium, such as a computer readable medium, for example, diskette, CD ROM, DVD, ROM, RAM, flash memory or hard disk. It could also comprise a series of computer readable instructions transmittable to a computer system, via a modem or other interface device, over either a tangible medium, including but not limited to optical or analogue communications lines, or intangibly using wireless techniques, including but not limited to microwave, infrared or other transmission techniques. The series of computer readable instructions embodies all or part of the functionality previously described herein.

Those skilled in the art will appreciate that such computer readable instructions can be written in a number of programming languages for use with many computer architectures or operating systems. Further, such instructions may be stored using any memory technology, present or future, including but not limited to, semiconductor, magnetic or optical, or transmitted using any communications technology, present or future, including but not limited to optical, infrared or microwave. It is contemplated that such a computer program product may be distributed as a removable medium with accompanying printed or electronic documentation, for example, shrink wrapped software, pre-loaded with a computer system, for example, on a system ROM or fixed disk, or distributed from a server or electronic bulletin board over a network, for example, the Internet or World Wide Web.

Certain preferred embodiments of the present disclosure will now be described in greater detail, by way of example only and with reference to the accompanying drawings, in which.

Figure 12:
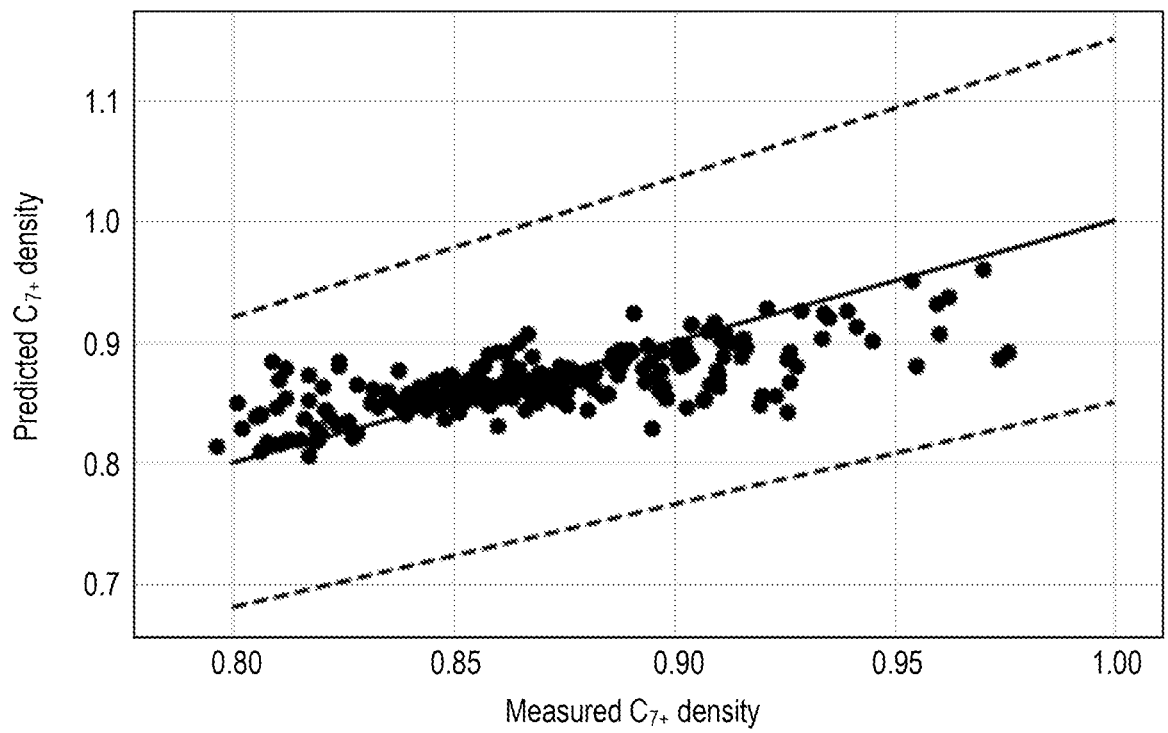
Figure 13:
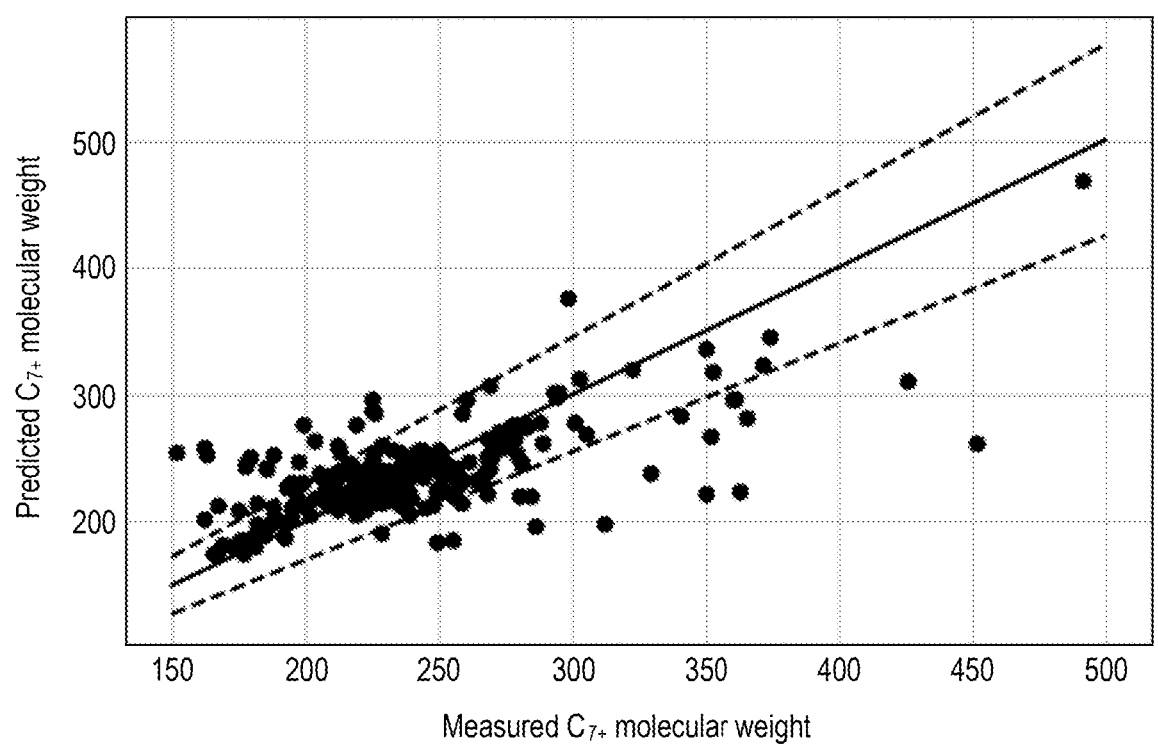

FIG. 12 is a graph showing a measured average density for $C_{7+}$ hydrocarbons (x-axis) and an average density for $C_{7+}$ hydrocarbons predicted using a model (y-axis) for a training data set; and FIG. 13 is a graph showing a measured average molecular weight for $C_{7+}$ hydrocarbons (x-axis) and an average molecular weight for $C_{7+}$ hydrocarbons predicted using a model (y-axis) for a training data set.

Drilling fluid is a fluid used to aid the drilling of boreholes into the earth. The main functions of drilling fluid include providing hydrostatic pressure to prevent formation fluids from entering into the well bore, keeping the drill bit cool and clean during drilling, carrying out drill cuttings, and suspending the drill cuttings while drilling is paused and when the drilling assembly is brought in and out of the hole.

Drilling fluids are broadly categorised into water-based drilling fluid, non-aqueous drilling fluid, often referred to as oil-based drilling fluid, and gaseous drilling fluid. The present disclosure is particularly applicable to liquid drilling fluid, i.e. water-based drilling fluid or non-aqueous drilling fluid, which are commonly referred to as "drilling mud".

Mud-gas logging entails gathering data from hydrocarbon gas detectors that record the levels of gases brought up to the surface in the drilling mud during a bore drilling operation.

Conventional mud-gas logging is used to identify the location of oil and gas zones as they are penetrated, which can be identified by the presence of gas in the mud system. This may be used to provide a general indication of the type of reservoir, as well as to determine where to take downhole fluid samples for more detailed analysis of the fluid composition.

The presence of hydrocarbon gas may be detected, for example, with a total gas detector.

Once the presence of hydrocarbon gas is detected, its composition may be examined for example with a gas chromatograph. The detection of the composition of the mud gas described below is sometimes referred to as "advanced mud-gas logging".

The most common gas component present is usually methane ($C_1$). The presence of heavier hydrocarbons, such as $C_2$ (ethane), $C_3$ (propane), $C_4$ (butane) and $C_5$ (pentane) may indicate an oil or a "wet" gas zone. Even heavier molecules, up to about $C_7$ (heptane) or $C_8$ (octane), may also be detectable, but are typically present only in very low concentrations. Consequently, the concentrations of these hydrocarbons are often not recorded.

The composition of the mud gas can be examined in order to provide predictions of the $C_1$ to $C_5$ concentrations within the reservoir fluid.

The measured mud-gas data is usually referred to as "raw" mud-gas data and is not comparable to the actual composition of the reservoir, since the mud gas contains gases that do not originate from the reservoir (e.g. gases present in the drilling mud or remaining from previous injection when recycling the drilling mud) and also because lighter hydrocarbon (e.g. $C_1$) are carried more easily by the drilling mud than heavier hydrocarbons (e.g. $C_2$ to $C_5$).

Firstly, a recycling correction is made to eliminate contamination of the gas by gases originating from previous injections of the drilling mud. This correction is applied based a separate mud-gas measurement that was taken before the drilling mud was injected into the drilling string.

Secondly, an extraction efficiency correction step is applied to increase the concentration of intermediate components (from $C_2$ to $C_5$), such that the mud-gas data after this step closely resembles a corresponding reservoir fluid sample composition.

The mud-gas-data after hydrocarbon recycling correction and extraction efficiency correction is usually referred to as "fully corrected" mud-gas data.

Alternatively, or additionally, the mud gas composition may be examined to estimate certain fluid properties of the reservoir fluid. For example, broad, empirical correlations exist to correlate the mud-gas composition against certain fluid properties of the reservoir fluid. For example, extremely dry gas reservoirs should give mud gas that comprises mostly $C_1$ and not much $C_{2+}$, e.g. with each of the $C_1/C_2$, $C_1/C_3$, $C_1/C_4$ and $C_1/C_5$ ratios (for the raw mud-gas data) being greater than 50. Wet gas reservoirs will often have ratios between 20 and 50, and oil reservoirs will have ratios between 2 and 20.

Whilst the above correlations broadly indicate the type of reservoir, it has previously not been possible to use the mud gas composition to provide precise predictions of the reservoir fluid properties.

The following technique allows for the accurate determination of certain properties of the reservoir fluid that are influenced by the oil composition of the reservoir fluid, based on the mud-gas data. Such reservoir fluid properties include the gas-oil ratio, the density of the reservoir fluid, the saturation pressure of the reservoir fluid, and the formation volume factor of the reservoir fluid.

Figure 1:
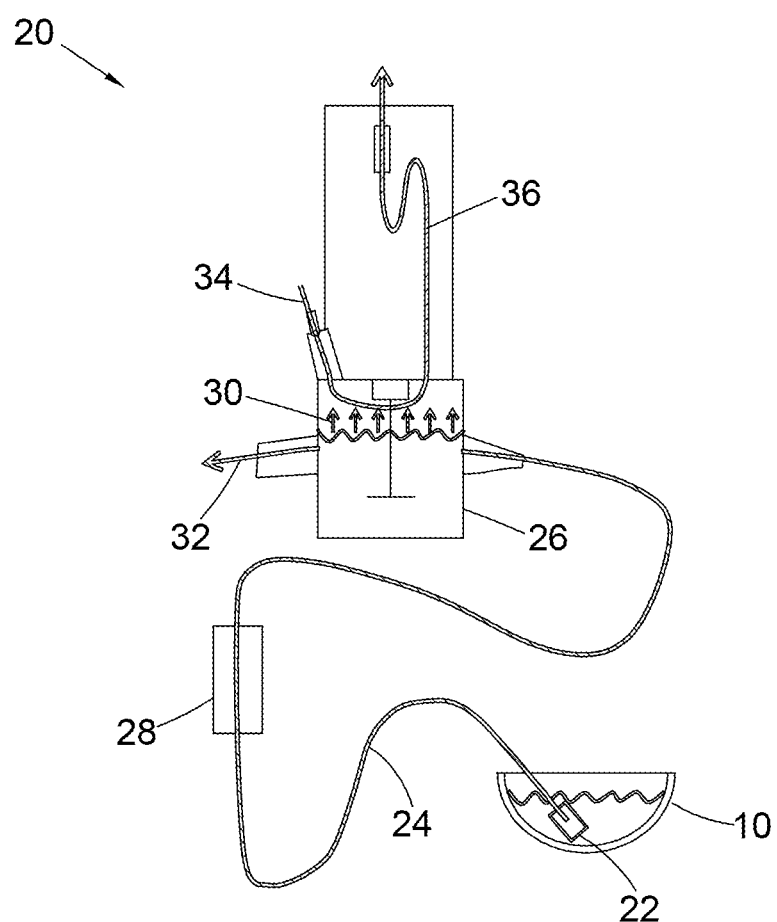
FIG. 1 is a schematic illustration of a mud-gas analysis tool.

An exemplary mud-gas analysis tool 20 is shown schematically in FIG. 1.

The tool 20 is coupled to a flow line 10 containing drilling mud returned from a borehole of a well. As discussed above, the drilling mud may be water-based mud or oil-based mud.

The tool 20 comprises a sampling probe 22 disposed with respect to the flow line 10 so as to collect a sample 24 of the drilling mud from the flow line 10. The drilling mud sample 24 is preferably a continuous sample, i.e. such that a portion of the flow of drilling mud within the flow line 10 is diverted through the mud-gas analysis tool 20.

The drilling mud sample 24 is supplied to a gas-separation chamber 26 where at least a portion of the gas carried by the drilling mud is released. The sample of drilling mud may be heated by a heater 28 upstream of the gas-separation chamber 26. Heating the drilling mud sample 24 helps to release the gas from the drilling mud sample 24. Typically, the mud sample 24 is heated to a temperature of around 80° C. to 90° C.

The released gas 30 is directed from the separation chamber 26 to a gas analysis unit (not shown), while the degassed mud 32 is returned to the flow line 10 or to another location for re-use.

The gas analyser may comprise a total gas detector, which may provide a basic quantitative indication as to how much gas is being extracted from the drilling mud by the tool 20. Total gas detection typically incorporates either a catalytic filament detector, also called a hotwire detector, or a hydrogen flame ionization detector.

A catalytic filament detector operates on the principle of catalytic combustion of hydrocarbons in the presence of a heated platinum wire at gas concentration below the lower explosive limit. The increasing heat due to combustion causes a corresponding increase in the resistance of the platinum wire filament. This resistance increase may be measured through the use of a Wheatstone bridge or equivalent detection circuit.

A hydrogen flame ionization detector functions on the principle of hydrocarbon molecule ionization in the presence of a very hot hydrogen flame. These ions are subjected to a strong electrical field resulting in a measurable current flow.

The gas analysis device may additionally or alternatively comprise an apparatus for detailed analysis of the hydrocarbon mixture. This analysis is usually performed by a gas chromatograph. However, several other detecting devices may also be utilised including a mass spectrometer, an infrared analyser or a thermal conductivity analyser.

A gas chromatograph is a rapid sampling, batch processing instrument that provides a proportional analysis of a series of hydrocarbons. Gas chromatographs can be configured to separate almost any suite of gases, but typically oilfield chromatographs are designed to separate the paraffin series of hydrocarbons from methane ($C_1$) through pentane ($C_5$) at room temperature, using air as a carrier. The chromatograph will report (in units or in mole percent) the quantity of each component of the gas detected.

A carrier gas stream 34, commonly comprising air, may be supplied to the separation chamber 26 and mixed with the released gas 30 to form a gas mixture 36 that is supplied to the gas analysis unit. The carrier gas stream 34 provides a continuous flow of carrier gas in order to provide a substantially continuous flow rate of the gas mixture 36 from separation chamber 26 to the gas analysis unit. Additionally, in the case of a gas analyser comprising a combustor, the use of air as the carrier gas may provide the necessary oxygen for combustion.

In some arrangements, the tool 20 may be configured to detect and/or remove $H_2S$ from the gas to prevent adverse effects that could influence hydrocarbon detection.

In some embodiments, non-combustibles gases, such as helium, carbon dioxide and nitrogen, can be detected by the gas analyser in conjunction with the logging of hydrocarbons.

Figure 2:
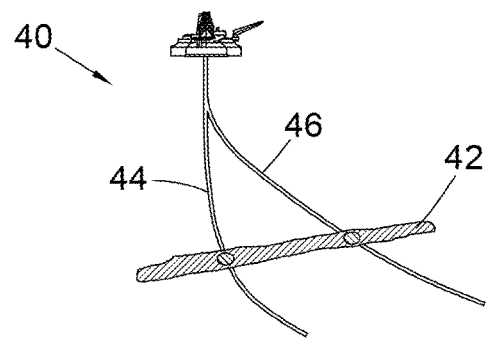
FIG. 2 is a schematic illustration of a well and a hydrocarbon-bearing reservoir.

FIG. 2 is a schematic example of a well site 40 comprising a reservoir 42 and two wells 44, 46. The first well 44 is drilled using a water-based drilling mud, and the second well 46 is drilled using an oil-based drilling mud.

Three fluid samples 48, 50, 52 have been taken from the well site 40.

The first sample 48 is a mud-gas sample taken from the first well 44. That is to say, the first sample comprises measurements of the concentration of $C_1$ to $C_5$ gases released by the water-based drilling mud.

The second sample 50 is a mud-gas sample taken from the second well 46. That is to say, the second sample comprises measurements of the concentration of $C_1$ to $C_5$ gases released by the oil-based drilling mud.

The third sample 52 is a wireline sample, taken directly from the reservoir 42.

Figure 3:
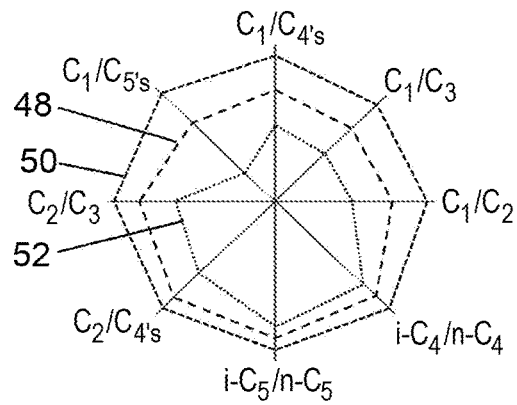
FIG. 3 illustrates a $C_1$ to $C_5$ hydrocarbon composition map for three samples taken from the well.

FIG. 3 is a geochemical radar chart showing raw (unadjusted) proportional gas compositions of the three samples 48, 50, 52. The geochemical radar chart in FIG. 3 displays the following composition ratios, from top position in clockwise order, $C_1/C_4$, $C_1/C_3$, $C_1/C_2$, i-$C_4$/n-$C_4$, i-$C_5$/n-$C_5$, $C_2/C_4$, $C_2/C_3$, $C_1/C_5$. The scales of the axes of the chart have been selected to maximise the space filled by the chart, i.e. such that the second sample 52 forms a regular octagon.

It should be noted that whilst the third sample 52 also comprises data relating to the oil content of reservoir, the ratios composing FIG. 3 are based only on the gas hydrocarbons, i.e. $C_1$ to $C_5$ hydrocarbons.

It will be apparent from FIG. 3 that whilst all three samples represent the same reservoir 42, the composition of the mud gas differs significantly from the gas composition of the reservoir fluid itself. Furthermore, the type of the drilling mud (and indeed its specific composition) also significantly affects the composition of the mud gas, as is apparent from comparison of the first sample 48 and the second sample 50.

Various, empirically derived relationships exist that can be used to correct the proportional compositions of the mud gas in order to estimate the corresponding proportional compositions of the gases within the reservoir.

Figure 4:
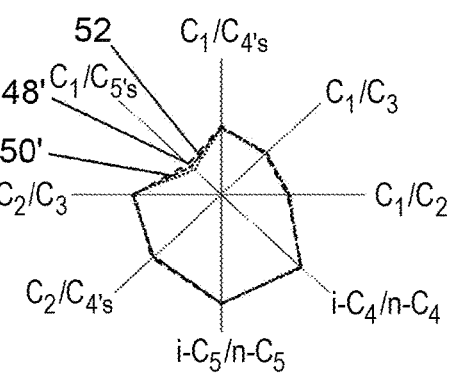
FIG. 4 illustrates a $C_1$ to $C_5$ hydrocarbon composition map for the three samples after a mud-gas correction has been applied.

FIG. 4 is a geochemical radar chart showing corrected (i.e. "fully corrected" data as discussed above) proportional gas compositions of the first and second samples 48, 50', together with the original proportional gas compositions of the third sample 52.

As can be seen from FIG. 4, the correction factors can be very effective for estimating the actual $C_1$ to $C_5$ compositional ratios of the reservoir fluid.

The following technique seeks to utilise a machine learning algorithm to produce a model that accurately estimates certain properties relating to the reservoir fluid, in particular the gas-oil ratio and the density of the reservoir fluid, based on the mud-gas data.

The general workflow for predicting the gas-oil ratio from mud-gas data comprises preparing and quality controlling a database containing reservoir sample data and mud-gas data, and training a machine learning model using the processed reservoir sample data from the database to predict the gas-oil ratio.

Figure 5:
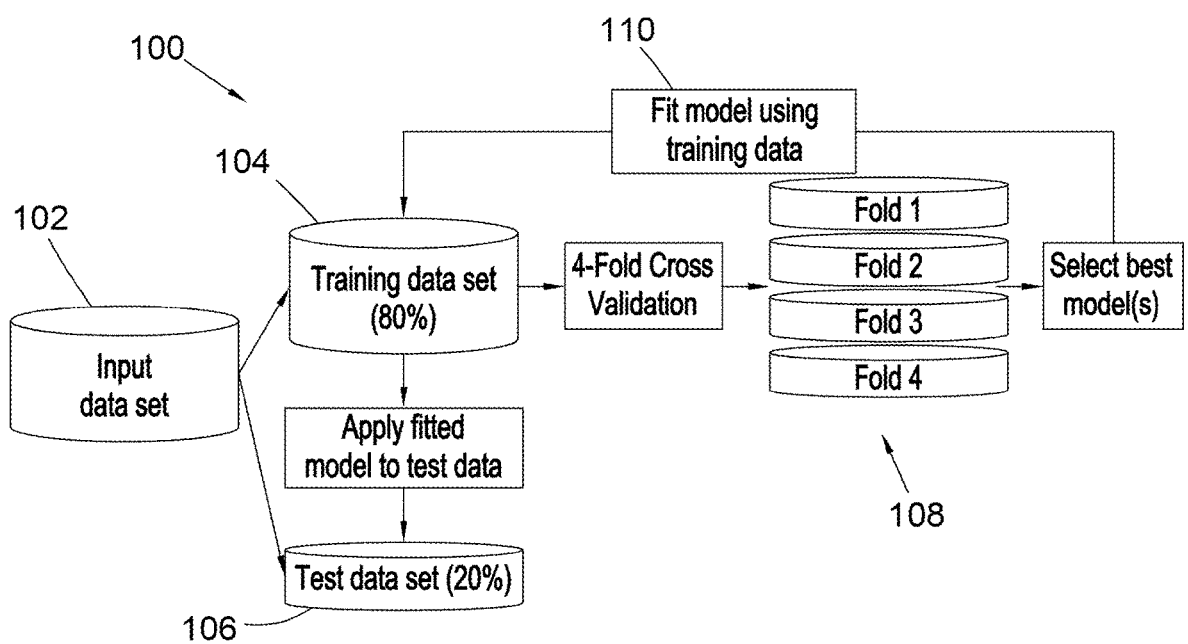
FIG. 5 illustrates a workflow for a machine learning algorithm to generate a first model for predicting a gas oil ratio using a training data set.

FIG. 5 illustrates a workflow 100 for training the machine learning algorithm in order to generate a model for prediction of a gas-oil ratio of a reservoir based on measured mud-gas data.

In the following example, an input data set 102 comprising data relating to 1153 reservoir samples was prepared. This input data set 102 was generated by pre-processing a larger, initial data set to generate suitable data for training the machine-learning algorithm.

The initial data set in this example comprises reservoir fluid properties data from more than 2000 reservoir fluid samples. Reservoir samples may be obtained, for example, by downhole fluid sampling. However, other techniques could also be used, for example by taking a sample of well fluid after the well has been completed.

Most of the reservoir fluid samples used in this analysis were from the Norwegian Continental Shelf (NCS), while the remaining samples were from international sites operated by Equinor®. The majority of the reservoir properties data from the NCS is public and can be accessed from oil field data published by the Norwegian Petroleum Directorate (NPD).

The reservoir fluid properties data should include at least hydrocarbon composition data, which may be either in the form of direct measurements of the concentration of each hydrocarbon component within the sample, typically covering $C_1$ to $C_{36+}$ hydrocarbons. In some embodiments, the concentration data may be in the form of relative data (e.g. as a ratio of compositions of different hydrocarbons) or may be otherwise normalised. The reservoir fluid properties data may optionally also include concentrations of one or more other constituents within the well.

The reservoir fluid properties data may include one or more derived properties of the reservoir fluid sample. Such derived properties may include the target property to be determined by the machine-learning algorithm, e.g. a gas-oil ratio in this case. Other derived properties may include a density of the fluid.

The reservoir fluid properties data is sometimes referred to as PVT data, as it is commonly obtained in a pressure-volume-temperature (PVT) laboratory, where researchers will employ various instruments to determine reservoir fluid behaviour and properties from the reservoir samples.

The initial data set for the machine learning algorithm 100 was first screened to remove reservoir samples that might skew the machine learning algorithm. This was performed using various quality control algorithms, which were applied either manually or algorithmically. Early attempts to generate models based on all of the reservoir samples within the initial data set, i.e. without this step, were found to be significantly less accurate in their predictions of the gas-oil ratio.

A first screening process was applied in order to identify and remove samples where the reservoir fluid properties data was not suitable for training the machine learning algorithm. The first screening process comprised a two-stage process.

The present inventors chose to examine single-flash gas-oil measurements, since these were the most commonly reported gas-oil measurement (1734 of the samples in the initial data set) and have standard reference conditions. Thus, any samples for which a single-flash gas-oil measurement was not available were removed.

Next, outliers were removed. To do this, a visual inspection and a manual verification process were carried out. Additionally, a target filter was applied which removed samples showing evidence of oil-based mud contamination, and also data with gas-oil ratio less than 10 $Sm^3/Sm^3$ or higher than 20 000 $Sm^3/Sm^3$.

After the first screening process, 1383 samples remained.

In some embodiments, the first screening process may be omitted.

A second screening process was then carried out comprising identifying and removing samples where biodegradation has occurred.

Under certain conditions, living microorganisms (primarily bacteria, but also yeasts, moulds, and filamentous fungi) can metabolize various hydrocarbons within a reservoir. This process is known as biodegradation and dramatically affects the composition and properties of the fluid. Different classes of hydrocarbon have different susceptibilities to biodegradation. The early stages of biodegradation are characterized by the loss of n-alkanes, followed by loss of acyclic isoprenoids. The remaining compound classes (e.g., highly branched and cyclic saturated hydrocarbons as well as aromatic compounds) are most resistant to biodegradation, but will also eventually be consumed.

The inventors have identified that the reservoir samples from biodegraded reservoirs consistently represent a 'branch' which behaves different than the trends from the majority of non-biodegraded reservoir samples. In particular, the normalized $C_1$ to $C_5$ composition of a biodegraded reservoir appears similar to that of a lean gas reservoir, but has a much higher gas-oil ratio. As mud gas is indicative of only the concentrations of these lighter hydrocarbons, biodegraded reservoir samples were found to cause significant errors in the prediction of gas-oil ratio by machine learning models.

Whilst biodegradation is a well-recognised phenomenon, its effects on mud-gas data had not previously been recognised. After excluding samples containing biodegraded oils from the reservoir fluid database, the remaining fluid samples were found to demonstrate a much stronger consistency.

Biodegradation of a reservoir sample can be identified either by a direct measurement for the microorganisms, or by analysis of the hydrocarbon composition of the reservoir fluid. Samples showing above a threshold level of biodegradation were removed from the training data set. In this example, any sample showing detectable biodegradation was excluded from the input data set 102. However, it will be appreciated that a permissible level of biodegradation may be appropriate in some situations, or where only a limited number of samples is available.

In the present example, approximately 20% of samples were removed during the second screening, leaving the 1153 "good" samples.

In some embodiments, the second screening process may be omitted.

Application of the above two types of screening was found to significantly improve the accuracy of the model generated by the machine-learning algorithm.

Next, the input data set 102 was generated from the initial data set for the samples that passed the screening.

The input data set 102 comprises reservoir fluid properties data for each sample. However, measured mud-gas data was not available for each sample. The inventors therefore investigated how closely the $C_1$-$C_5$ composition predicted by correction of the measured mud-gas data, where available, correlated to the actual $C_1$-$C_5$ composition of the corresponding reservoir fluid sample.

The analysis indicated that there were no significant distributional differences between the composition of corrected mud-gas data and composition of the reservoir fluid properties data. When considering the mud-gas data and the reservoir fluid properties data at the level of independent observations, good correlation was also present. Several outliers were present. However, these cases were each identified as samples having low quality mud-gas data, as will be discussed in greater detail later.

This supports the idea that a machine learning model can be built based on the reservoir fluid properties data, which could then be used to predict a gas-oil ratio from measured mud-gas data.

The measured mud-gas data comprises measured hydrocarbon composition data for gas released from the drilling fluid from the sample location.

It will be appreciated that there is a lag-time between the drill bit passing through the sample location, and when the mud reaches the surface and is analysed. However, workers in this field will be familiar with the procedures for calculating the lag time to determine the depth to which the mud-gas sample corresponds. Therefore, this will not be discussed in detail.

The composition data for the mud-gas preferably comprises data for at least $C_1$ to $C_4$ hydrocarbons, and preferably at least $C_1$ to $C_5$ hydrocarbons (as is the case in the present example). In some cases, concentrations for up to $C_7$ or greater hydrocarbons may be included.

The composition data may be stored either as a direct measurement of concentration (e.g. measured in ppm or similar units), or alternatively as a relative concentration (e.g. as a proportion of another hydrocarbon, usually $C_1$). In some embodiments, the composition data may be normalised.

The mud-gas data may comprise data relating to the drilling operation, such as the type of drilling fluid used. Alternatively, or additionally, the composition data may be stored in an adjusted form, e.g. having been pre-corrected to give equivalent estimations of the gas composition of the sample itself.

The input data set 102 comprises target data and input data for each sample that passed the screening. The target data corresponds to the desired output of the model. The input data corresponds to the data that will be input into the eventual model.

The target data in this example is a gas-oil ratio, and in this example is the single-flash gas-oil measurement of the sample. As discussed above, this data was stored as part of the reservoir properties data within the initial data set. Alternatively, other measurements of gas-oil ratio may be used, or a gas-oil ratio may be derived from the reservoir composition data, i.e. based on the concentrations of the various hydrocarbons.

The input data is mud-gas data, i.e. data indicative of the composition of gases released from the drilling fluid from the sample location. Preferably, the data used is corrected mud-gas data, as discussed previously, i.e. such that the model is independent of factors such as the type of drilling mud used.

The input data may be the measured mud-gas data for the sample. However, as discussed above, this was not available in many cases and it has been found that corrected measured mud-gas data corresponds closely to the respective hydrocarbon composition of the reservoir properties data for the sample. Thus, the input data may use predicted data, i.e. predicted, corrected mud-gas data, which corresponds to the concentrations of the lighter hydrocarbons from the reservoir properties data.

In this example, the input data for each sample comprised the concentrations of $C_1$ to $C_5$ hydrocarbons from the reservoir fluid properties data for the sample.

It should be noted that the composition data may be provided in any suitable form, such as a direct measurement of concentration, a relative concentration, or a normalised concentration.

Next, a model generation is performed, in which a model is generated and validated based on the input data set 102.

The input data set 102 is first divided into a training data set 104 and a testing data set 106. The input data set 102 is preferably curated such that at least the testing data set 106 contains data that spans the various classes of the input data set 102 as a whole (e.g. dry gas reservoirs, wet gas reservoirs, oil reservoirs).

Typically, at least 50% of the input data set 102 should be used for training, and at least 10% of the input data set 102 should be used for testing. Common ratios include 50:50, 70:30, 75:25, 80:20, 90:10. However, it will be appreciated that other divisions may be used instead.

Generally the larger the training data set, the more accurate the model will be. However, if too small a test data set is used (or indeed if no test data set is used) then it is not possible to confidently verify the accuracy of the model, e.g. making it difficult to detect an over-fitted model (only accurate for the specific training data).

In this example, all samples from wells that did not have measured mud-gas data were used to form the training data set 104, and the samples with measured mud-gas data were used to form the testing data set 106. As a result, the training data set 104 included about 80% of the input data set 102 (i.e. 922 samples) and the testing data set 106 included the other 20% of the input data set 102 (i.e. 231 samples).

To generate a model, a machine learning algorithm is provided with the training data set 104, and a set of training parameters to control the machine learning algorithm.

The inventors identified that a Gaussian Process algorithm was the most accurate model, followed by Universal Kriging, Random Forest, KMean and Elastic Net. However, it will be appreciated that any suitable algorithm may be used. Those operating within this field will be familiar with the procedures for selecting and utilising a machine learning algorithm. Therefore, this will not be discussed in detail.

Model validation 108, e.g. cross-validation, may then then be performed. During the model validation 108, the model is tested to determine how well it predicts new data that was not used in estimating the model, in order to flag problems such as over fitting or selection bias. Model validation 108 is an optional step.

Cross-validation involves partitioning the training data set 104 into complementary subsets, performing the model fitting using one subset of the training data set 104, and validating the analysis on the other subset of the training data set 104. To reduce variability, most methods use multiple rounds of cross-validation, performed using different partitions, and the validation results are combined (e.g. averaged) over the rounds to give an estimate of the model's predictive performance (e.g. a mean average prediction error, MAPE).

In this example K-fold cross-validation, and particularly 4-fold cross-validation is used. In K-fold cross-validation, the training data 104 is separated in K disjoint subsets (in this case, four), known as "folds". Then, cross-validation is performed by training the model on all of the data except for one fold, and validating the trained model using the fold that was not used for training. The best model is then selected as the model having the best predictive performance, e.g. the lowest MAPE.

Figure 6:
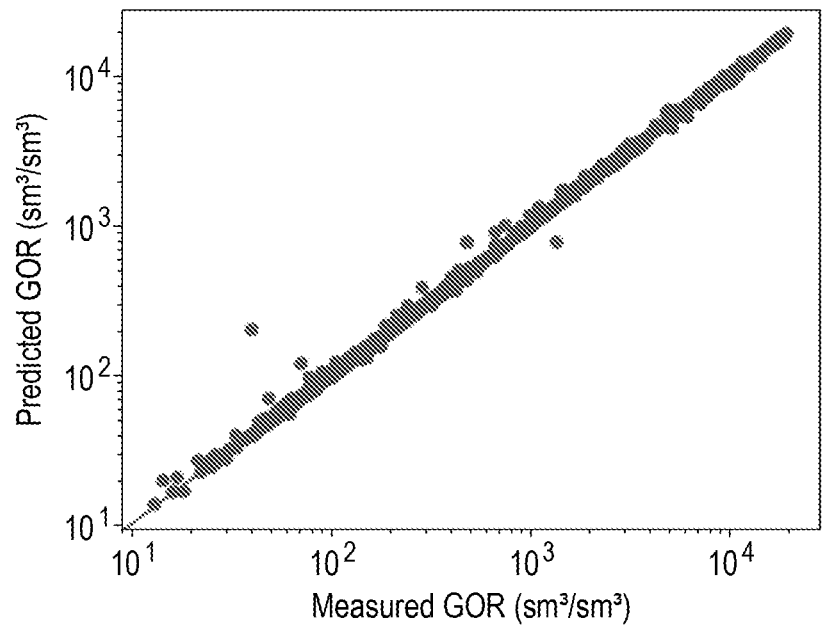
FIG. 6 is a graph showing an observed gas-oil ratio (x-axis) and a gas oil ratio predicted using the first model (y-axis) for the training data set.

A first testing step 110 is then performed, in which the model is tested using the training data set 104 as a whole. The results of the first testing step 110 is shown in FIG. 6. As can be seen, the gas-oil ratio predicted by the model (x-axis) closely corresponds to the actual gas-oil ratio (y-axis) of the sample.

A second testing step 112 is then performed, in which the model is tested using the test data set 106. As discussed previously, this is a curated set of data that is broadly representative of the data as a whole, and was not used during the generation of the model.

Figure 7:
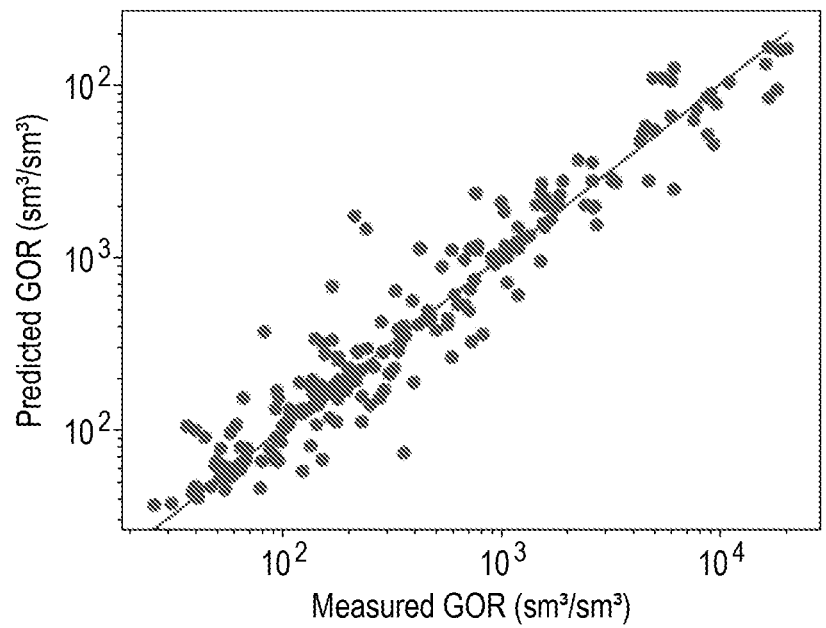
FIG. 7 is a graph showing an observed gas-oil ratio (x-axis) and a gas oil ratio predicted using the first model (y-axis) for a first testing data set, which has been pre-screened.

The results of the second testing step 112 is shown in FIG. 7. As can be seen, whilst the correlation between the gas-oil ratio predicted by the model (x-axis) and the actual gas-oil ratio (y-axis) of the sample is less closely correlated than in FIG. 6, there is still a good correlation between the results, indicating that the model provides effective prediction of the gas-oil ratio based on measured mud-gas data.

The model has been found to predict a gas-oil ratio of the reservoir fluid based on $C_1$ to $C_5$ mud-gas data with MAPE of about 36% for the screened test data. This is acceptable for predictions made during the drilling phase, as such predictions were not previously possible.

It was further found that the gas oil ratio prediction accuracy could be improved significantly if any additional oil-related information is available in the drilling phase or wireline operations. For example, a second model for gas-oil ratio prediction was generated in a pressure gradient (indicative of fluid density) was added as an additional parameter of the input data.

Figure 8:
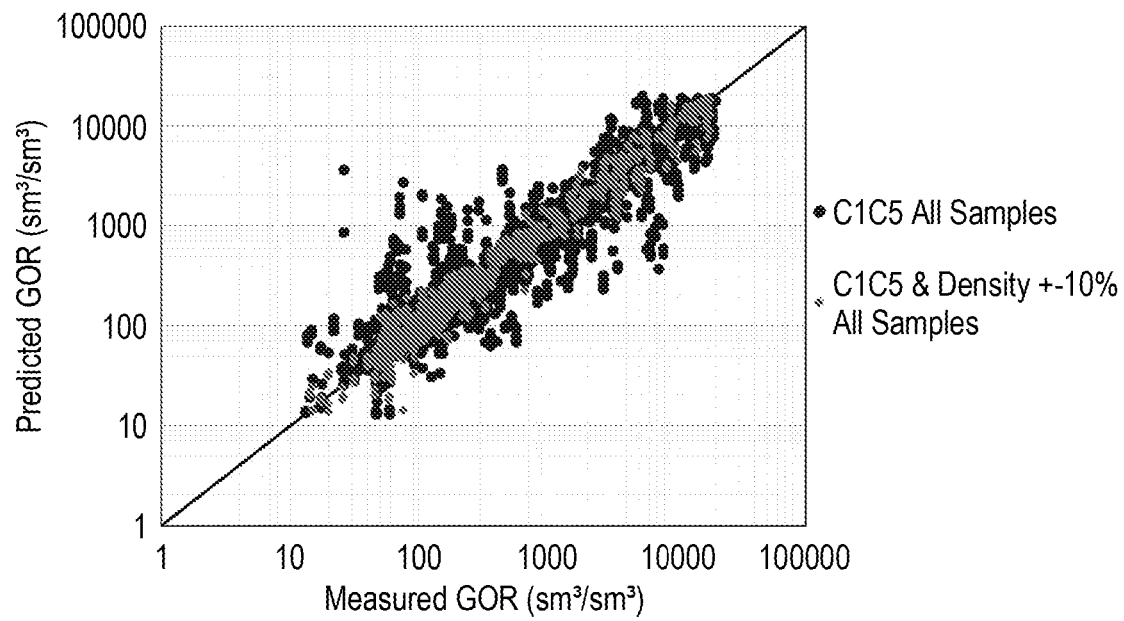
FIG. 8 is a graph showing is a graph showing an observed gas-oil ratio (x-axis) and a gas oil ratio predicted using the first model or using a second model (y-axis) for the testing data set.

The results of the application of the second model to a testing data set are shown in FIG. 8, together with the results of the first model applied to the same testing data set. The MAPE of the second model dropped to 15%, even when allowing for a 10% error in the pressure gradient.

Understanding the quality of the measured mud-gas data is important before performing a fluid property (e.g. gas-oil ratio) prediction because the mud-gas data quality will significantly impact prediction accuracy. The following characteristics of the mud-gas data values have been identified as indicating low quality or unreliable data:

Large fluctuations of a component within a small depth range.

First observations after missing measurements.

$C_1$ content below a given threshold.

$C_4$ or $C_5$ content below a given threshold.

To quantify the quality of the mud-gas data, the inventors derived a quality control metric (QC metric) which ranged from 0 to 1. High quality mud-gas data would have QC metric value close to 1. If one or more of the above factors are found, then the QC metric would be reduced. Low-quality mud-gas data was indicated by QC metric close to 0. A single numeric quality measure between 0 and 1 can be plotted side-by-side with a predicted fluid property log (as will be discussed below) to visualize the confidence level associated with each prediction, based on mud-gas data quality.

Figure 9:
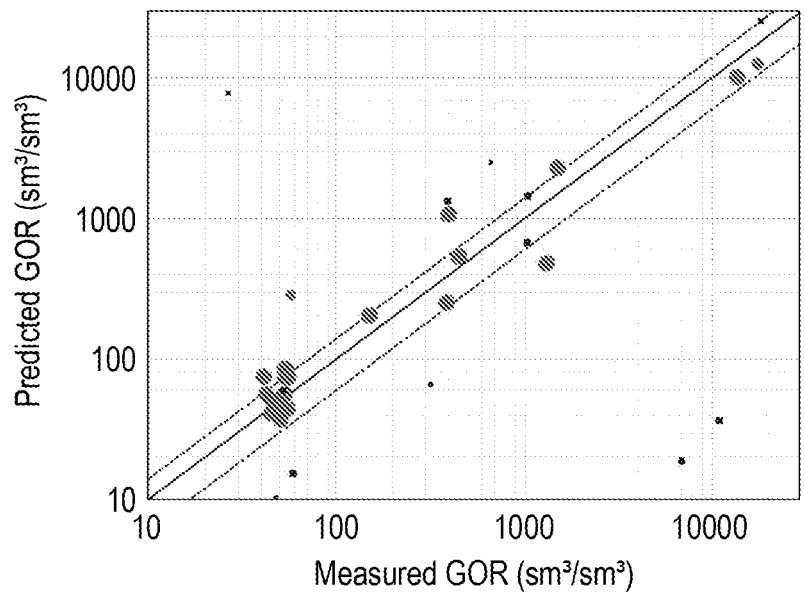
FIG. 9 is a graph showing an observed gas-oil ratio (x-axis) and a predicted gas oil ratio (y-axis) for second testing data set, which has not been pre-screened.

FIG. 9 is a graph showing measured gas-oil ratio (x-axis) against a gas-oil ratio predicted using the first model (y-axis) for a representative selection of samples of test data set. In this graph, the size of the data point indicates the QC metric value for that sample, with samples having a QC metric above 0.3 shown in grey and samples having a QC metric below 0.3 shown in black. The 40% MAPE boundaries are also illustrated in the graph.

As can be seen, the samples having a higher QC metric correspond closely, whilst samples having a lower QC metric have poor correspondence. Thus, these factors provide a useful indication of the accuracy of a prediction of the gas-oil ratio.

As discussed above, different classes of hydrocarbon have different susceptibilities to biodegradation. In particular, n-alkanes are more susceptible to biodegradation than i-alkanes. $C_4$ and $C_5$ hydrocarbons are present in gas phase as both butane and isobutene and pentane and isopentane, respectively, which can be separately identified by the mud-gas logging tool 20. Thus, by examination of the i-$C_4$/n-$C_4$ and i-$C_5$/n-$C_5$.ratio, it is possible to estimate whether biodegradation has occurred (with a high i-$C_4$/n-$C_4$ ratio or high and i-$C_5$/n-$C_5$ ratio indicating likely biodegradation).

This may be included either as part of the QC metric analysis, or may be provided separately.

Mud-gas data is generated continuously during the drilling process. Therefore, by applying the machine learning model to the mud-gas data, it is possible to provide, at an early stage of the well installation procedure, a continuous log for the well bore of the predicted reservoir property, e.g. gas-oil ratio or fluid density. This is something that has not been possible previously until much later in the process.

Figure 10:
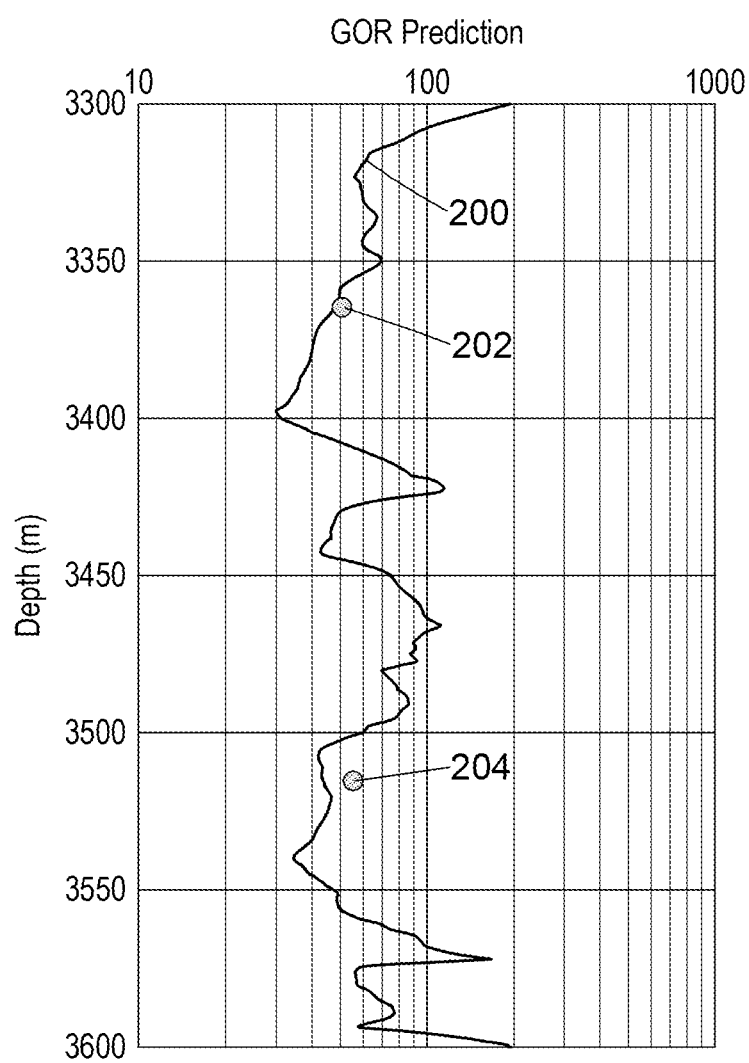
FIG. 10 is a graph showing a continuous log of predicted gas-oil ratio for a well, determined using the model, as well as measured point-value gas-oil ratios.

FIG. 10 shows a gas-oil ratio log 200 generated using the first model generated above based on measured mud-gas data collected as the well was drilled through the region of interest. Furthermore, two fluid samples 202, 204 were taken using downhole fluid analysis, and precise measurements of the gas-oil ratio were determined. As can be seen, these closely correspond to the gas-oil ratio values determined based on the mud-gas data. However, the mud-gas data log provides much more detail regarding the composition of the reservoir than would have been available from these samples 202, 204 alone.

Whilst fluid property logs generated based on mud-gas data alone are useful, particularly because they will be available at an early stage of the proceedings, it is desirable to further increase the accuracy of these logs. Thus, in some embodiments, the fluid property log may be calibrated following the taking of subsequent samples, for example using the downhole fluid samples 202, 204.

In one embodiment, one or more downhole fluid samples 202, 204 may be taken providing an indication of the fluid property. The continuous fluid property log may then be adjusted based on a value of the fluid property derived from these samples. For example, a shift may be applied to the log so as to align the fluid property value of the log with a measure value of the fluid property indicated by the downhole fluid samples.

Where multiple samples are taken, the shift to be applied to the log between the sample locations may be calculated by interpolation of the shifts applied at each sample location.

This technique provides a highly precise, continuous log of a desired fluid property of the reservoir.

Whilst the above examples have been described in the context of a gas-oil ratio as the target reservoir fluid property, the same technique may also be employed to create a model for estimating other reservoir fluid properties of the reservoir fluid at a sample location, based on measured mud-gas data. Exemplary reservoir fluid properties include a fluid density of the reservoir fluid, a saturation pressure of the reservoir fluid, and a formation volume factor of the reservoir fluid.

In one example, two models were generated for the prediction of the fluid density of the reservoir fluid, based on measured mud-gas data. One model was generated for predicting stock tank oil density (i.e. after flashing the fluid to nominal atmospheric storage pressure and temperature), and another model was generated for predicting live reservoir fluid density (i.e. at reservoir pressure and temperature). Both models were generated in substantially the same manner as discussed above in respect of the first model for gas-oil ratio prediction.

These models were found to predict the density of the fluid within the reservoir based on measured $C_1$ to $C_5$ mud-gas data with a MAPE of about 3% for the stock tank oil density and a MAPE of about 5% for the live reservoir fluid density.

Furthermore, a similar technique has also been used to train a model to estimate the reservoir fluid composition and corresponding $C_{7+}$ fraction properties. This is advantageous, as this information can be used to for an equations of state (EOS) model calculation. The EOS model for a particular fluid is an expression that describes the relationship between pressure, temperature and volume of the fluid and can be used to predict the phase behaviour of the fluid in order to derive further properties thereof.

It is normally considered necessary to know at least the following properties of the fluid in order to determine the equations of state:

1) The absolute composition of each of the $C_1$ to $C_6$ hydrocarbons and the absolute composition of the $C_{7+}$ hydrocarbons combined;
2) The average hydrocarbon density of the $C_{7+}$ hydrocarbons; and
3) The average hydrocarbon molecular weight of the $C_{7+}$ hydrocarbons.

When determining the equations of state for a fluid, the $C_{7+}$ hydrocarbons are usually grouped together because these hydrocarbons usually remain in the liquid/oil phase. A standard $C_{7+}$ characterisation method can split the $C_{7+}$ into multiple pseudo components for EOS calculation.

It will now be shown that each of these properties can be determined using the machine learning models discussed above, thus allowing the EOS model to predict all reservoir fluid properties at the sample location.

Figure 11:
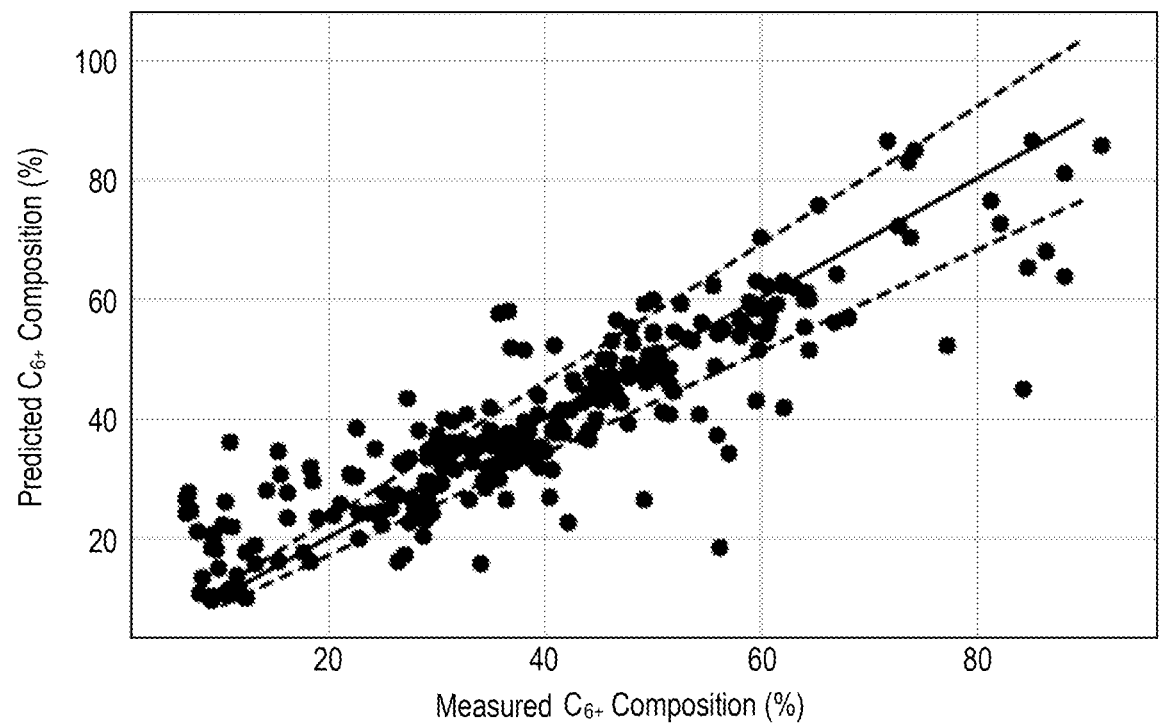
FIG. 11 is a graph showing a measured $C_{6+}$ composition (x-axis) and a $C_{6+}$ composition predicted using a model (y-axis) for a training data set.

FIG. 11 shows a graph illustrating test data for a machine learning model that was used to estimate an absolute composition for $C_{6+}$ hydrocarbons within the reservoir fluid. That is to say, the percentage of the reservoir fluid that is composed of $C_6$ or higher hydrocarbons. From this value, combined with the mud-gas data which can be used to determine the relative compositions of the $C_1$ to $C_5$ hydrocarbons, it is possible to determine the absolute (percentage) compositions of each of the $C_1$ to $C_5$ hydrocarbons.

A similar model (not shown) is then determined for estimating an absolute composition for $C_{7+}$ hydrocarbons within the reservoir fluid, which can be used to calculate the absolute (percentage) composition of $C_6$ hydrocarbons when combined data from the model used in FIG. 11.

Thus, it is possible to estimate the absolute composition of each of the $C_1$ to $C_6$ hydrocarbons and the absolute composition of the $C_{7+}$ hydrocarbons combined.

FIG. 12 shows a graph illustrating test data for a machine learning model that was used to estimate an average density (shown as a specific gravity) of the $C_{7+}$ hydrocarbons.

FIG. 13 shows a graph illustrating test data for a machine learning model that was used to estimate an average molecular weight of the $C_{7+}$ hydrocarbons.

As can be seen, all of the models show a good accuracy for the prediction of these properties, suggesting that the use of such machine models should produce good approximations to apply the EOS model for reservoir fluid property prediction.

Although individual fluid property models (like density and GOR) were developed in the first examples, it will be appreciated that a physical model could be generated that would calculate all fluid properties. The EOS model approach in the second example demonstrates a good solution for predicting all reservoir fluid properties.

Whilst preferred embodiments have been described above, it will be appreciated that these have been provided by way of example only, and the scope of the invention is to be limited only by the following claims.

The invention claimed is:

1. A method of generating a model for predicting a value of at least one fluid property of a fluid at a first sample location within a hydrocarbon reservoir, comprising:
providing an initial data set relating to a first plurality of second sample locations, the initial data set comprising reservoir fluid properties data for each second sample location;
selecting a second plurality of second sample locations as a subset of the first plurality of second sample locations, the selection being based on a degree of biodegradation of a fluid at the first sample location;
generating an input data set from the initial data set comprising input data and target data, the input data comprising mud-gas data, or a derivative thereof, for the second plurality of second sample locations, and the target data comprising the at least one property of the hydrocarbon reservoir for each of the second plurality of second sample locations; and generating a model using a correlation between the input data and the target data such that the model can be used to predict the at least one property of the fluid at the first sample location based on measured mud-gas data for the first sample location;

providing measured mud-gas data for the first sample location;

predicting the values of a fluid property of the fluid at the first sample location by supplying the measured mud-gas data to the model;

determining whether the fluid has been biodegraded by comparison of a ratio of i-C4/n-C4 from the measured mud-gas data to a predetermined threshold and/or a ratio of i-C5/n-C5 from the measured mud-gas data to a predetermined threshold; and providing an indication of confidence associated with the predicted value of the fluid property for the second sample location, wherein the indication of confidence is based on whether the fluid at the first sample location has been biodegraded.

2. A method according to claim 1, wherein providing the measured mud-gas data comprises:

processing a drilling fluid used whilst drilling through the first sample location to release hydrocarbon gases from the drilling fluid; and analysing the released hydrocarbon gases to determine their composition, wherein the measured mud-gas data indicates a concentration of the released hydrocarbon gases.

\* \* \* \* \*